US00PP25688P2

(12) United States Plant Patent
Kordes

(10) Patent No.: US PP25,688 P2
(45) Date of Patent: Jul. 14, 2015

(54) HYBRID TEA ROSE PLANT NAMED 'KORMACCAP'

(50) Latin Name: *Rosa hybrida*
Varietal Denomination: KORmaccap

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 195 days.

(21) Appl. No.: 13/987,442

(22) Filed: Jul. 24, 2013

(51) Int. Cl.
*A01H 5/00* (2006.01)

(52) U.S. Cl.
USPC ..... Plt./137

(58) Field of Classification Search
USPC ..... Plt./137, 130
See application file for complete search history.

(56) References Cited

PUBLICATIONS

Pluto Plant Variety Database Mar. 30, 2015 p. 1.*

* cited by examiner

*Primary Examiner* — Annette Para

(57) ABSTRACT

A new and distinct variety of rose with long lasting, novel pastel pink flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORmaccap'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1998. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORmaccap'.

SUMMARY OF THE INVENTION

The new rose plant may be distinguished from its seed parent, an 'un-named seedling', by the following combination of characteristics:

1. 'KORmaccap' has a pastel pink flower, whereas the 'un-named seedling' has a dark pink flower.

2. 'KORmaccap' has a cluster flower formation, whereas the 'un-named seedling' has mostly a sole flower formation.

The new rose plant may be distinguished from its pollen parent, an 'un-named seedling', by the following combination of characteristics:

1. 'KORmaccap' has a strong fragrance, whereas the 'un-named seedling' has no fragrance.
2. 'KORmaccap' has a very double petal count, whereas the 'un-named seedling' has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORmaccap' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORmaccap' was selected in May 1999 from the seedling beds to be asexually propagated for further evaluation. The first asexual propagation of 'KORmaccap' was done by budding in July 1999 at the inventor's nursery in Offenseth-Sparrieshoop, Germany.

These initial and other subsequent propagations conducted in controlled environments demonstrate that 'KORmaccap' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORmaccap'.

DETAILED BOTANICAL DESCRIPTION

The following is a description of 'KORmaccap', as observed growing in June 2013 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORjuknei', a rose variety from the same inventor described and illustrated in U.S. Plant Pat. No. 22,499 and issued on Feb. 21, 2102 are compared to 'KORmaccap' in Chart 1.

CHART 1

| Characteristic | 'KORmaccap' | 'KORjuknei' |
|---|---|---|
| Receptacle shape | Urn-shaped | Funnel-shaped |
| Fragrance | Very strong; citrus and fruity | Moderate; spicy |
| Prickle incidence | 12 prickles per 10 cm of stem | 20-25 prickles per 10 cm of stem |

Parents:

*Seed parent*.—An 'un-named seedling'.

*Pollen parent*.—An 'un-named seedling'.

Classification:

*Botanical classification*.—*Rosa hybrida* 'KORmaccap'.

*Commercial classification*.—Hybrid Tea rose.

FLOWER AND FLOWER BUD

Blooming habit: Recurrent. Floriferous.

Flower bud:

*Size*.—Upon opening, 35 mm in length from base of receptacle to distal end of bud and 30 mm diameter at its widest point.

*Bud form*.—Short. Pointed ovoid.

*Bud color*.—As sepals first unfold, bud color is White Group N155D. When ¼ open, the upper surface of petals is White Group N155D, and the lower surface is White Group N155D. Guard Petals are White Group 155D with intonations of Yellow-Green Group 145D in basal area of petal and Red-Purple Group 58A in the marginal zone of guard petal.

*Sepals*.—Color: Upper surface Yellow-Green Group 147C. Lower surface Yellow-Green Group 146C. Intonations of Greyed-Purple Group 184B on lower surface. Size: Average 20-25 mm (l)×12 mm (w). Shape: Weak foliaceous appendages on some sepals. Apex: Apiculate. Base: Flat at union with receptacle. Quantity: Five. Surface texture: Upper side: Moderately pubescent. Lower surface: Smooth with stipitate glands in upper zone. Margins: Pubescent with stipitate glands.

Flower bloom:

*Fragrance*.—Very strong. Citrus and fruity.

*Duration*.—On the plant 3-5 days. As a cut flower, 3-4 days. Senesced petals drop away cleanly.

*Size*.—Medium for a hybrid tea rose. When open, the average flower diameter is 60-70 mm and the average flower height is 35 mm.

*Form*.—Shape of flower when viewed from the side: Upon opening, upper part: Flat. Upon opening, lower part: Flat. Open flower, upper part: Flattened convex. Open flower, lower part: Flattened convex.

Color:

*Upon opening, petals*.—Outermost petals: Outer Side: White Group N155D. Inner Side: White Group N155D. Innermost petals: Outer Side: Red Group 38C. Inner Side: Red Group 38B.

*Upon opening, basal petal spots*.—Basal petal spot, outermost petals: Outer Side: Green-Yellow Group 1D. Inner Side: Green-Yellow Group 1D. Basal petal spot, innermost petals: Outer Side: Green-Yellow Group 1C. Inner Side: Green-Yellow Group 1B.

*After opening, petals*.—Outermost petals: Outer Side: White Group N155D. Inner Side: White Group N155D. Innermost petals: Outer Side: Red Group 38D. Inner Side: Red Group 38D.

*After opening, basal petal spots*.—Basal petal spot, outermost petals: Outer Side: Green-Yellow Group 1C. Inner Side: Yellow Group 2D. Basal petal spot, innermost petals: Outer Side: Yellow Group 2C. Inner Side: Yellow Group 2B.

General tonality: On open flower Red Group 38D. No change in the general tonality at the end of the 3rd day. Afterwards, general tonality is White Group N155D.

Petals:

*Petal count*.—Very Double.

*Average range*.—Approximately 75 petals under normal conditions.

*Petal reflex*.—Weak.

*Petal margin*.—Entire.

*Petal shape*.—Obovate to obtuse. Apex: Obtuse. Base: Obtuse.

*Petal size*.—20-35 mm (l)×20-30 mm (w).

*Thickness*.—Thin.

*Petal arrangement*.—Not formal.

*Texture*.—Smooth.

Petaloids:

*Petaloid count*.—Average of 3-10 per flower.

*Petaloid size*.—5-25 mm (l)×4-15 mm (w).

*Petaloid color*.—Inner side: Red Group 38D. Outer side: Red Group 38D.

*Petaloid texture*.—Smooth.

*Margins*.—Entire.

*Petaloid shape*.—Variable, oval to spatulate. Apex: Obtuse. Base: Attenuate to obtuse.

Reproductive organs:

*Pistils*.—Abundant. Approximately 40 present. Stigmas: Location: Slightly inferior in position to anthers. Color: Greyed-Yellow Group 163C. Styles: Length: About 8 mm long. Color: Yellow-Green Group 145C.

*Stamens*.—Approximately 80 on average and regularly arranged. Anthers: Size: Average 4 mm (l)×1 mm (w).

Pollen: Generally present. Color: Greyed-Orange Group 165A. Filaments: Color: Yellow Group 2C. Length: 8-10 mm.

Receptacle:

*Color*.—Yellow-Green Group 144B. Intonations of Greyed-Purple Group 183C.

*Shape*.—Urn-shaped.

*Texture*.—Smooth.

*Size*.—12 mm (h)×15 mm (w).

Peduncle:

*Surface*.—With stipitate glands.

*Length*.—60-70 mm average length.

*Diameter*.—2-3 mm average diameter.

*Color*.—Yellow-Green Group 146D. Intonations of Greyed-Orange Group 176A on 90% of peduncle.

*Strength*.—Strong.

*Texture*.—Smooth.

*Borne*.—Singularly. Flowers pendant to upright.

THE PLANT

Growth: Moderately vigorous.

Plant habit: Upright to bushy. When grown as a field plant, the average plant height is 120 cm and the average plant width is 80 cm.

Stems:

*Stem color*.—Young wood: Yellow-Green Group 146C. Older wood: Yellow-Green Group 146D.

*Intonations*.—Greyed-Orange Group 176B. Intense anthocyanin on young wood with 80% coverage.

*Stem surface texture*.—Young wood: Smooth. Older wood: Smooth.

Prickles: Present.

*Incidence*.—Average of 12 per each 10 cm of stem.

*Size*.—Average length: 8 mm.

*Color*.—Immature prickles: Greyed-Red Group 182B. Mature prickles: Greyed-Red Group 182A.

*Shape*.—Deeply concave.

Leaves: Normally 5 leaflets on normal leaves in middle of the stem.

*Venation pattern*.—Pyramidal net pattern.

*Leaf size*.—150 mm (l)×110 mm (w).

*Abundance*.—Average.

Leaflets:

*Size*.—Average size of the terminal leaflet is 60 mm (l)×45 mm (w).

*Shape*.—Ovate. Base: Obtuse. Apex: Acute

*Margins*.—Finely serrated.

*Surface*.—Upper: Semi-glossy. Lower: Matte.

*Texture*.—Upper side of leaflet: Leathery. Under side of leaflet: Leathery.

*Color, mature foliage*.—Upper Leaflet Surface: Green Group 137A. Lower Leaflet Surface: Yellow-Green Group 147B.

*Color, juvenile foliage*.—Upper Leaflet Surface: Yellow-Green Group 146A. Lower Leaflet Surface: Yellow-Green Group 146B.

*Anthocyanin intonation*.—Greyed-Purple Group 183C on margin and lower side.

*Arrangement*.—Odd pinnate.

*Venation*.—Reticulate.

Stipules:

*Size*.—25 mm (l)×12 mm (w).

*Stipule color*.—Yellow-Green Group 146B.

*Anthocyanin*.—Greyed-Red Group 182A on upper mid rib, less prominent on lower side.

*Stipitate glands*.—Limited number on margins.

*Texture*.—Smooth.

*Shape*.—Apex: Apiculate. Base: Winged.

Petiole:

*Length*.—Average 20-25 mm.

*Diameter*.—Average 3 mm.

*Petiole color*.—Yellow-Green Group 146A. Underneath: Yellow-Green Group 146C.

*Prickles*.—Present on underside.

*Stipitate glands*.—Limited number on margin of upper side.

*Texture*.—Smooth.

Petiole rachis:

*Length*.—Average 20-25 mm.

*Diameter*.—Average 3 mm.

*Color*.—Yellow-Green Group 146B.

*Margins*.—Limited number of stipitate glands.

*Prickles*.—A few small prickles underneath at leaflet attachment.

*Texture*.—Smooth.

Hips/seed formation: None observed.

Winter hardiness: To date, the variety has been grown successfully in Zone 5.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

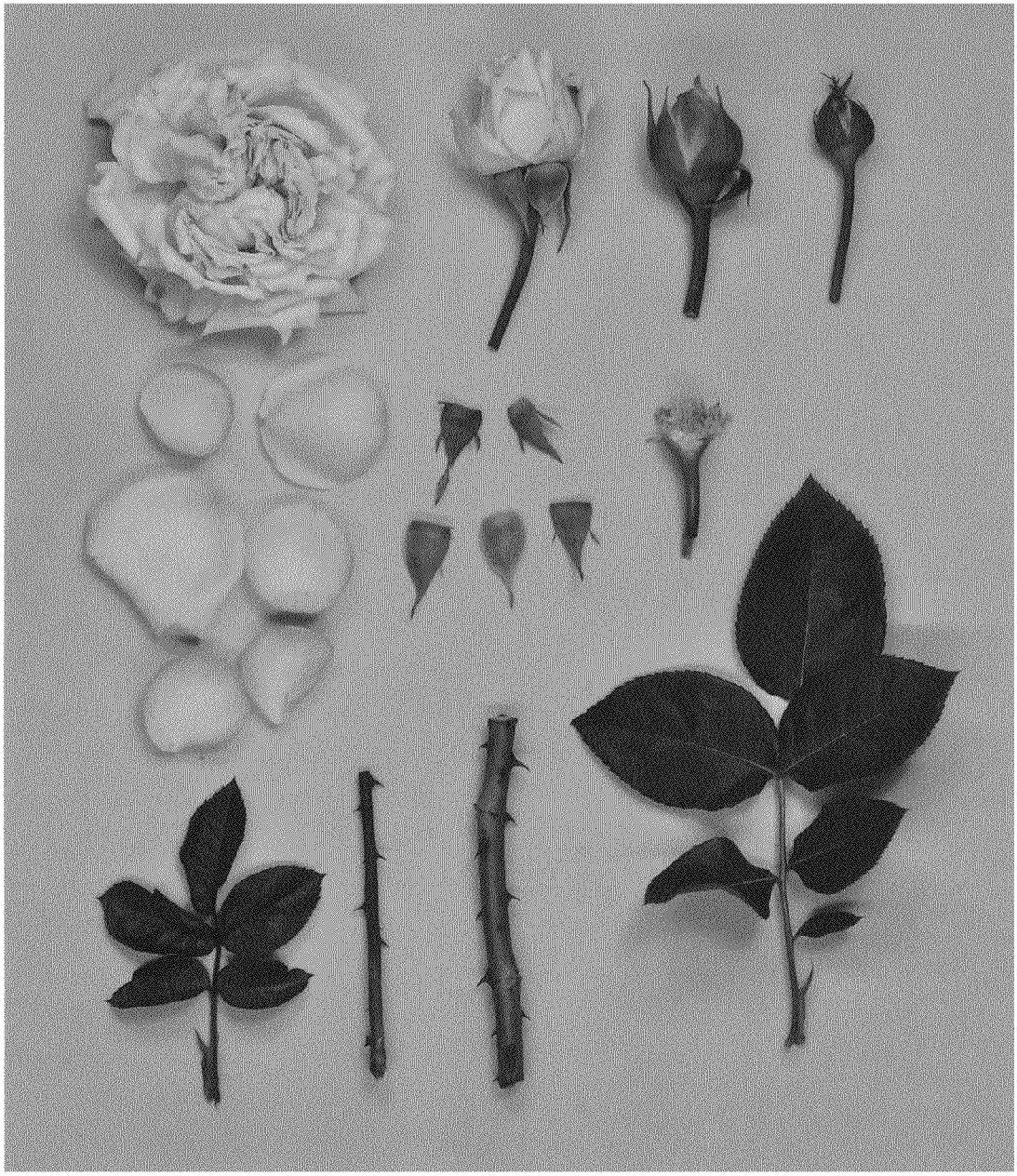

* * * * *